US006204276B1

(12) United States Patent
Veselovsky et al.

(10) Patent No.: US 6,204,276 B1
(45) Date of Patent: Mar. 20, 2001

(54) DICARBOXYLIC GERMANIUM COMPLEX AND ITS THERAPEUTIC USE

(75) Inventors: Vladimir Vsevolodovich Veselovsky; Leonid Leonidovich Danilov; Serguey Dmitrievich Maltsev; Alexander Vasilyevich Pronin; Alexander Naumovich Narovlyansky; Alexander Vladimirovich Sanin; Anna Valentinovna Deyeva; Aleftina Mikhailovna Amchenkova, all of Moscow (RU)

(73) Assignee: Primamedic Ltd., Limassol (CY)

( * ) Notice: Subject to any disclaimer, the term of this patent is extended or adjusted under 35 U.S.C. 154(b) by 0 days.

(21) Appl. No.: 09/254,354

(22) PCT Filed: Sep. 5, 1997

(86) PCT No.: PCT/GB97/02408

§ 371 Date: Mar. 5, 1999

§ 102(e) Date: Mar. 5, 1999

(87) PCT Pub. No.: WO98/09975

PCT Pub. Date: Mar. 12, 1998

(30) Foreign Application Priority Data

Sep. 19, 1996 (EP) .................................................. 96306462

(51) Int. Cl.[7] .......................... A61K 31/44; C07D 213/79
(52) U.S. Cl. ........................... 514/354; 546/326; 546/327
(58) Field of Search .................................... 546/326, 327; 514/354

(56) References Cited

FOREIGN PATENT DOCUMENTS 0652223 5/1995 (EP) .

OTHER PUBLICATIONS

Section Ch, Week 8820 "New di:pyridine bis–salicyclic acid germanium —useful in treatment of cancer, allergies, hypertension, bronchial asthma, etc." Derwent Publications Ltd., London, GB; Class B03, AN 88–136366, XP002023935 & JP 63 077 888 A (UBE Industries KK), Apr. 8, 1988 (abstract).

Section Ch, Week 8928 "Basic aminoacid and amine salts of 3–oxy:germyl:propionic acid polymer —are used as active components of immune activator" Derwent Publications Ltd., London, GB; Class A96, AN 89–201984, XP002023936 & JP 01 139 587 A (Sanwa Kagaku Kenkyusho), Jun. 1, 1989 (abstract).

Section Ch, Week 8347 "Tetrakis (1–(N–carboxy methyl carbamoyl)ethyl mercapto) germanium —is useful in treating cancers, inflammatory diseases and in skin conditioning" Derwent Publications Ltd., London, GB; Class B05, AN 83–823287, XP002023937 & JP 58 174 391 A (Dai–Ichi Yakuhin SA), Oct. 12, 1983 (abstract).

Deng–Hai *et al.* (1993) "Synthesis of five coordinate spiro-cyclic germanium (IV) complex diethanol amine"*J. Chinese Chemical Society* 40:373–377.

*Primary Examiner*—Jane Fan
(74) *Attorney, Agent, or Firm*—Saliwanchik, Lloyd & Saliwanchik

(57) ABSTRACT

A germanium complex of germanium and an aromatic or nono-aromatic, carbocyclic or heterocyclic dicarboxylic acid, e.g. germanium bis(pyridine-2,6-dicarboxylate) has anti-infectious, interferon-inducing, and immunomodulating activity.

5 Claims, No Drawings

DICARBOXYLIC GERMANIUM COMPLEX AND ITS THERAPEUTIC USE

This is a 371 of PCT/GB97/02,408 now WO 98/09,975

FIELD OF THE INVENTION

The invention relates to anti-infectious immunomodulating preparations which may find application in human and veterinary medicine.

BACKGROUND OF THE INVENTION

The preservation of homeostasis and resistance to the influence of environmental factors such as infectious agents is determined to a large extent by the functioning of the systems (first of all, the immune system) ensuring nonspecific resistance of the organism. The interferon system is one of the most important parts of non-specific immunity. Interferons are cytokines by means of which intercellular and humoral reactions directed to the preservation of the homeostasis of the organism occur (Gresser, Cell Immunol., 977, .43, No. 2, pp.406-413; Stewart, The Interferon System, Springer-Verlag, N.Y. ,1979; Soloviov et al, Interferons in Medical Theory and Practice, M., Medizina, 1981, p400) The interferon system is an assemblage of cell elements capable of producing different kinds of interferon, changing its functional status by the action of interferon and thereby realizing intercellular and humoral reactions ensuring the preservation of homeostasis of the organism. Defects in the interferon system lead to disorders in the function of the immune system and, as a consequence, to an increased risk of the development of severe infectious and oncological diseases. A selective modulation with interferons, interferon inducers or other immunomodulators of certain parts of the immune system directly participating in protection against one or another disease may result in correction of immuno- and interferon deficiency and greatly enhances the resistance of the organism to infectious diseases. (The Biology of the Interferon System. 1988. Proceedings of the Fifth Annual meeting of the International Society for Interferon Research (ISIR 88), Kyoto, Japan, 14–18 November, 1988, Tokyo, 1989, p.503).

A new group of preparations—interferon inducers -has found wide use as infection control and immunomodulating preparations. Interferon inducers comprise a heterogeneous group of high and low molecular compounds of natural and synthetic origin. Such preparations possess a wide spectrum of biological activity: anti-infectious, anti-tumor, immunomodulating, radiation protection, etc. (Ershov et al, Interferon and Inducers Thereof, M., Medizina, 1980, p.173).

There are known preparations of alpha-, beta- and gamma-interferons which, according to the technology of preparation are divided into natural (interferons of the first generation) and recombinant (interferons of the second generation):
1. Natural interferons: preparations of α-interferon- human leukocyte interferon, egiferon, villferon; preparations of β-interferon—human fibroblast interferon, feron; γ-interferon—human immune interferon.
2. Recombinant interferons: preparations of α-interferon-reaferon, realdiron, roferon; preparations of α2b-interferon—intron, inrek; preparations of α2c-interferon—berofor; preparations of β-interferon—beta-feron; preparations of γ-interferon—gamma-feron (Cheknev et al, Interferon System Normally and in Pathologic Conditions, M., Medizina, 1966, pp.196–221).

A significant short-coming of natural interferons lies in the method of obtaining them from human blood which involves the risk of transmission of heterologous genetic information and viral infections. Recombinant interferons have no such short-comings and are quite valuable in specific clinical situations. However, the presence of only one interferon subtype in each specific preparation limits the range of their use. All interferon preparations induce exogeneous interferonization of the organism which is their common limitation.

There are known interferon inducers used in the clinical practice: synthetic compounds such as, for example, amixin (a low molecular compound of the aromatic series, belonging to the class of fluorenones), neovir (a low molecular compound belonging to biobasic heteroaromatic compounds, to acridinones class). Natural compounds are known, such as, for example, megasin (the product of gossypol -condensation via aldehyde group with β-sodium aminoethylsulphuric acid), larifan (double-stranded RNA of phage λ2); ridostine (double stranded RNA obtained from a lysate of killer yeasts *Saccharomyces cerevisiae*) (Ershov et al, Antiviral Drugs. St. Petersburg, 1993, p.104). The advantage of this group lies in the capacity of inducing autologous interferons. The above-mentioned interferon inducers, however, induce the synthesis of alpha- and beta-interferons only. At the present time, no sufficiently effective inducers of gamma-interferon suitable for use in the clinical practice are known.

Germanium-organic compounds are known to possess different kinds of biological activity. There is a preparation known as carboxyethylgermanium-sesquioxide of the general formula $[GeCH_2CH_2COOH]_2O_3$ which is capable, upon oral administration, of inducing interferon production in the blood of mice. Later, the preparation was demonstrated to be capable of inducing γ-interferon synthesis in a suspension of mononuclear cells in vitro (Munakata et al, Interferon Res., 1987, v.7, pp.69–76). However, it has toxicity and low effectiveness as an immune interferon inducer. The raw material (germanium-chloroform) for its production is scarce.

The germanium complex 2, 6-pyridinediyl-biscarbonylox-(hydroxypropoxygermanium), possessing the properties of an immune interferon inducer, is described by Ignatenko et al in Russian Inventor's Certificate No. 1622989 of 22.09.90. This substance, however, has a narrow spectrum of the immunomodulating activity.

Thus, it was important to develop a new preparation possessing anti-infectious, interferon-inducing, and immunomodulating activity which could be used in human and veterinary medicine for prevention and treatment of infectious diseases, immuno- and interferon-deficient conditions and which would lack the above-mentioned defects of the known analogues.

SUMMARY OF INVENTION

Germanium complexes according to the present invention are of a saturated or non-saturated, carbocyclic or heterocyclic dicarboxylic acid, the two carboxylic acid groups being relatively in the 1 and 3 positions on the ring. The ring may have 0, 1 or 2 heteroatoms, e.g. N, 0 or S. It may have 4, 5, 6 or 7 members. A specific embodiment of this invention is germanium bis(pyridine-2,6-dicarboxylate) of formula I:

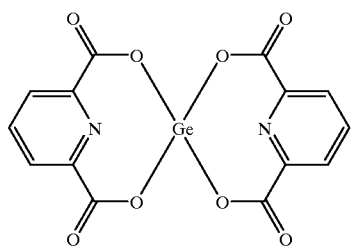

I

The new compounds possess anti-infectious, interferon-inducing, and immunomodulating activities which may be used in human and veterinary medicine for prevention and treatment of infectious diseases, immuno- and interferon-deficient conditions.

DESCRIPTION OF THE INVENTION

The novel complexes may be produced by reacting the acid, e.g. 2,6-pyridinedicarboxylic acid, with a tetraalkoxygermanium, preferably tetramethoxygermanium or tetraethoxygermanium. The tetraalkoxygermanium may be formed directly in the reaction mixture, for instance, from a germanium tetrahalide and an alkali metal alcoholate, e.g. germanium tetrachloride and sodium (m)ethanolate (obtained by dissolving metallic sodium in (m)ethanol).

The reaction may be performed in an organic solvent medium such as hexane, heptane, methanol or ethanol; the reaction temperature is usually within the range of 60° to 90° C. The reaction is preferably performed under an inert gas atmosphere such as argon or nitrogen, the reaction time being about 3–5 hours. The target product is recovered by conventional methods, for instance, filtration and drying in vacuum, for example, at 1 torr at 40° C.

The invention also provides a pharmaceutical composition containing as the active ingredient an effective amount of the germanium complex with a pharmaceutically acceptable carrier, excipient, or diluent. The pharmaceutical composition may be administered by different routes such as oral, parenteral, intranasal, etc.

For oral application, the composition may be used in the form of tablets, aqueous suspensions, dispersed powders or granules, as well as syrups or elixirs. The compositions intended for oral administration may be obtained by any method known in the art used for preparation of pharmaceutical compositions. Such compositions may contain one or more agents selected from sweeteners, aromatizers, dyeing agents and preservatives used for pharmaceutical preparations possessing good aesthetic and taste qualities.

The tablets may contain the active ingredient in a mixture with non-toxic pharmaceutically-acceptable excipients which are commonly used for preparation of tablets. Said excipients may be inert diluents such as calcium carbonate, sodium carbonate, lactose, calcium phosphate, granulating and disintegrating agents, for example, maize starch, cellulose derivates or alginic acid.

The tablets may have no coating or be coated by known methods, e.g. with a membrane delaying the process of decomposition thereof in the gastrointestinal tract, exerting thereby a prolonged effect. Aqueous suspensions may contain the active ingredient in a mixture with excipients suitable for the preparation of aqueous suspensions.

Pharmaceutical compositions for parenteral administration, for instance, subcutaneous or intramuscular, may comprise sterile injection solutions in water or physiological saline. For intranasal administration, the pharmaceutical composition may comprise a solution of the germanium complex in water or physiological saline solution.

As will be clear to those skilled in the art, the dose of complex to be used will depend upon the desired effect, e.g. immunomodulating, interferon-inducing, anti-infectious, as well as upon the degree of the seriousness of the disease, age and condition of the patient. Usually, a single dose is from 0,05 mg/kg to 100 mg/kg. The number of administrations may vary from 1 to 4 per day.

The novel complex has low toxicity. In investigations of acute toxicity in mice, the $LD_{50}$ is 900 mg per kilo body weight.

Specific examples of obtaining the germanium-organic compound of formula I, the physico-chemical characteristics thereof, examples of pharmaceutical compositions based thereon, as well as the results of biological trials thereof are presented below.

The structure of the obtained compound has been confirmed by the data of spectral analysis (IR, $^1$H and $^{13}$C NMR, mass), the purity was proved by the element analysis data.

The IR spectra of germanium bis(pyridine-2,6-dicarboxylate) were obtained on the apparatus "Bruker IFS 113v". The $^1$H NMR and $^{13}$C NMR were obtained on the spectrometer "Bruker AC-200". Mass-spectra (EU) were obtained on the apparatus "Finnigan AT Incos 50" at 70 eV.

EXAMPLE 1

6,4 g (0,038 mol) 2,6-pyridinedicarboxylic acid, 4,0 g (0,02 mol) tetramethoxygermanium and 25 ml absolute methanol under a nitrogen atmosphere were heated under reflux with vigorous stirring at the boiling point of the solvent (64° C.) for 3 hours. The sediment was filtered in a Shott filter, washed with methanol (2×10 ml) and dried at a temperature of 40° C. in vacuum (1 torr) for 3 hours. The yield was 6.88 g (90%) of the compound based on 2,6-pyridinedicarboxylic acid.

The obtained compound comprises colourless crystal needles with a melting temperature of 303–305° C. (decomposition). It is moderately soluble in water, diethylformamide and dimethyl sulphoxide, and insoluble in hydrocarbons, chloroform, ether, ethanol.

IR (ν, cm⁻, tablets in KBr): 667, 768, 922, 1095, 1148, 1304, 1368, 1493, 1600, 1732, 3097, 2800–3100.

1H NMR (δ, ppm, 200,13 MHz,$D_2O$): 8,35 (m, 6H, H-aromatic).

$^{13}$C NMR(δ, ppm, 50,32 MHz, $D_2O$): 129,7 (β-C), 143,2 (γ-C), 147,8 (α-C), 167,4 (C=O).

Mass-spectrum (m/z), ($^{74}$Ge): 360 [M-$CO_2$]+, 272, 228, 195, 171, 154, 139, 122, 112, 93, 84, 77.

Elemental analysis for $C_{14}H_6GeN_2O_8$:

Found, %: C 41,47; H 1,68; Ge 17,86; N 6,60.

Calculated,%: C 41,75 ; H 1,50; Ge 18,02; N 6,95.

Molecular weight 402,76.

EXAMPLE 2

To 1,1 g (0,048 mol) Na and 25 ml of absolute methanol at room temperature under an atmosphere of nitrogen were added 2,6 g (0,012 mol) tetrachlorogermanium during 5 min. The reaction mass was heated under reflux for 1,5 hours, then cooled to 20° C. The precipitate (NaCl) was filtered in a Shott filter and washed with methanol (3×15 ml). To the resulting filtrate comprising tetraethoxygermanium solution in ethanol, 3 g (0,18 mol) of 2,6-pyridinedicarboxylic acid were added. Further procedure was as described in Example 1. The yield was 3,45 g (95%) based on 2,6-pyridinedicarboxylic acid.

The spectral characteristics of the compound obtained in this way are essentially the same as those described above in example 1.

EXAMPLE 3

A solution for injection was prepared by dissolving germanium bis(pyridine-2,6-dicarboxylate) in water at room temperature. One ampoule of this solution contains:
germanium bis(pyridine-2,6-dicarboxylate) 0,01 g
water for injection 2 ml

EXAMPLE 4

Tablets were prepared by triturating the components in a mortar and forming in the pressing machine. One tablet contains:
germanium bis(pyridine-2,6-dicarboxylate) 25 mg
sodium methylcellulose 350 mg
sucrose 125 mg Investigation of induction of α, β, γ interferons in mouse serum in vivo Male CBA mice weighing 12–14 g were inoculated intraperitoneally with the compound I in the form of an aqueous solution in doses of 0,005–50 mg/kg. The level of interferon synthesis in the blood serum was determined at various intervals (5, 24, 48, 72 hours). Interferon titrations were carried out in L-929 cell cultures. The test virus was mouse encephalomyocarditis virus. The results are presented in Table 1.

TABLE 1

| Dose (mg/kg) | Interferon activity post-inoculation (units/ml) | | | |
| --- | --- | --- | --- | --- |
| | 5 hrs | 24 hrs | 48 hrs | 72 hrs |
| 0.05 | 320 | 320 | 160 | 80 |
| 0.5 | 1280 | 640 | 160 | 1280 |
| 5.0 | 160 | 40 | 160 | 40 |
| 50.0 | 640 | 160 | 10 | 320 |

As will be seen from Table 1, compound I induced serum interferon production, within the first 5 hours postinoculation interferons α and β being detectable, and at later intervals γ interferon. The optimal dose of the compound is 0,5 mg/kg.

Investigation of the effect on cell sensitivity to interferon (a) Human diploid fibroblast cell culture (M-19) highly sensitive to interferon was seeded into wells of a 96-well plate in Eagle's medium with 10% calf embryo serum. On the 3rd day of growth the culture was inoculated with compound I in a concentration of μg/ml. After 24 hours of incubation (37° C., 5% $CO_2$), titrations of α-interferon (reaferon with initial activity $2 \times 10^6$ IU/ml against 100 TCD of vesicular stomatitis virus) were carried out. The sensitivity of the cells to interferon was determined by the cytopathic effect of the virus. The results are presented in Table 2.

(b) Cells of the continuous line J-41 with reduced sensitivity to α-interferon were seeded into 96-well plates in a concentration of $10^5$ cells/ml in medium 199 with 10% embryo calf serum. Next day compound I was added to the cultures in a concentration of 1 μg/ml. Interferon titrations and determination of the sensitivity thereto were carried out as described above in (a).

TABLE 2

| Cell Culture | Interferon titre ($1 \times 10^6$ IU/ml) | |
| --- | --- | --- |
| | Control | Compound I |
| M-19 | 2.0 | 16.0 |
| J-41 | 0.02 | 0.08 |

As will be seen in Table 2, after 24-hour treatment of M-19 cells with compound I, the sensitivity of the cells to α-interferon (reaferon) increased 8-fold. After 24-hour treatment of J-41 cells with compound I their sensitivity to interferon increased 4-fold.

The above results indicate that compound I may be used in clinical practice for correction of the interferon and enhancement of sensitivity of the patients to interferon preparations.

Investigation of the effect on hemopoietic stem cell

Compound I was diluted in physiological saline solution to a concentration of 2,5 or 0,5 μg/ml. Mice of the experimental groups were inoculated with 0,2 ml of one of the obtained solutions (0,5 and 1 μg/mouse respectively) intraperitoneally. Control animals were given injections of physiological saline solutions. At 1, 2, 3, 4 and 7 days after administration of the test compound, the animals were given heparin (40 units/mouse), and then specimens of the peripheral blood, spleen and bone marrow from thighbones. The blood was diluted 1:1 with physiological saline solution. Bone marrow and spleen suspensions were prepared by the standard method. The content of hemopoietic stem cells (HSC) in the blood, bone marrow and spleens of the animals treated with the preparation were tested by the method of exogenous colony formation in the spleen of syngeneic lethally irradiated recipients; more specifically, diluted peripheral blood (0,1 ml), bone marrow cells (3–5 $\times 10^4$ cells) or spleen cells ($5 \times 10^5$ cells) were inoculated to lethally irradiated syngeneic recipients which were killed at 8–9 days; their spleens were removed, fixed in Bouin's solution, and the number of visible plaques or colonies developing from HSC was counted.

For the determination of the effect of the preparation on proliferation of HSC, suspensions of bone marrow or spleen cells were treated in vitro with oxyurea in a concentration of 1 mg/ml for 2 hours at 37° C. before inoculation into irradiated recipients. The number of HSC going into S-phase was determined by the formula $A=(a-b) \times 100/a$, wherein a is the number of HSC colonies without oxyurea treatment and b is the number of HSC colonies treated with oxyurea. The results are presented in Table 3.

TABLE 3

| | Coefficient of stimulation of HSC release into the blood | | | | | |
| --- | --- | --- | --- | --- | --- | --- |
| | Time of bleeding | | | | | |
| Dose (μg/mouse) | 7 days | 4 hrs | 1 day | 2 days | 3 days | 4 days |
| 0.5 | 3.2 | 1.5 | 7.1 | 2.6 | 5.2 | 3.7 |
| 1.0 | 4.7 | 3.2 | 7.5 | 3.3 | 2.1 | 1.6 |

As may be seen in Table 3, compound I increases the number of HSC in the blood. No capacity to stimulate HSC release into the S-phase was demonstrated.

Investigation of the staphylococcal activity

The preparation was inoculated subcutaneously to CBA mice in doses from 0,1 to 10 μg per mouse, after which the animals were inoculated with 1,25×10⁶ microbial cells of *Staphylococcus aureus* Wood 46. The survival rate was determined as a percentage of that in the control group of mice which received no compound I. The results were respectively 39.8%, 60.0% and 80.7% at 0.1, 1.0 and 10.0 μg doses. Thus, a dose of 1 μg enhances the resistance of mice to staphylococcus.

Investigation of anti-influenza activity

The model system was an experimental influenza infection in mice caused by the laboratory WSN strain of influenza A virus (H1N1). The virus had been grown in 9-day-old chick embryos. Mice C57B1/6 anesthesized with ether were inoculated intranasally each with 50 μl LD50 of the virus diluted 1:100. The preparation was inoculated in a dose of 100 μl (20 μg/mouse) intramuscularly on the day of infection. The control group of the animals received a placebo solution. Each group consisted of 10 male mice weighing 14–16 g. The deaths of the animals were recorded every day for 14 days, and at the end of the experiment the average survival time and lethality were determined. The data are presented in Table 4.

TABLE 4

| Groups | Lethality (%) | Average survival time (M ± m) |
|---|---|---|
| Control | 100 | 4.6 ± 0.4 |
| Preparation | 70 | 7.3 ± 1.6 |

The above data show a high anti-influenza effect.

Investigation of clinical effectiveness in dogs with distemper

Dogs with an established diagnosis of distemper (duration of the disease from 10 to 30 days; in 3 animals—the intestinal form of the disease, in 2- pulmonary form, and in 3 animals—the neuro-paralytic stage) were inoculated intramuscularly with 2–4 ml (depending on the animal's weight) of 0,5% solution of the test compound I in distilled water twice daily for 3–10 days. After this course of treatment all the animals became clinically normal.

What is claimed is:

1. A 1:2 complex of germnanium and a dicarboxylic acid, wherein said complex is germanium bis(pyridine-2,6-dicarboxvlate).

2. The complex according to claim 1, wherein said complex has the formula of compound (I)

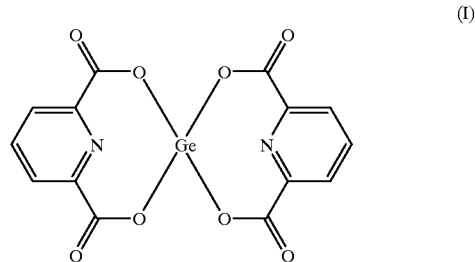

3. A pharmaceutical composition comprising a complex according to claim 1 and an inert carrier, excipient or diluent, for use in therapy.

4. A method for treatment of an infection or condition mediated by the induction of interferon or by imunomodulation, wherein said condition is influenza, said method comprising administering an effective amount of a complex of claim 1 to a person or animal in need of treatment.

5. A process for preparing a complex according to claim 1, which comprises the reaction of a tetraalkoxygermanium with said acid.

* * * * *

UNITED STATES PATENT AND TRADEMARK OFFICE
CERTIFICATE OF CORRECTION

PATENT NO. : 6,204,276 B1
DATED : March 20, 2001
INVENTOR(S) : Vladimir Vsevolodovich Veselovsky, Leonid Leonidovich Danilov, Serguey Dmitrievich Maltsev, Alexander Vasilyevich Pronin, Alexander Naumovich Narovlyansky, Alexander Vladimirovich Sanin, Anna Valentinovna Deyeva, Aleftina Mikhailovna Amchenkova It is certified that error appears in the above-identified patent and that said Letters Patent is hereby corrected as shown below:

Column 8,
Line 6, "germnanium" should read -- germanium --.
Line 8, "dicarboxvlate" should read -- dicarboxylate --.

Signed and Sealed this

Sixth Day of November, 2001

Attest:

NICHOLAS P. GODICI
Attesting Officer   Acting Director of the United States Patent and Trademark Office